US011020017B2

(12) United States Patent
Govari et al.

(10) Patent No.: US 11,020,017 B2
(45) Date of Patent: Jun. 1, 2021

(54) ANGIOPLASTY GUIDEWIRE

(71) Applicant: BIOSENSE WEBSTER (ISRAEL) LTD., Yokneam (IL)

(72) Inventors: Assaf Govari, Haifa (IL); Yaron Ephrath, Karkur (IL); Vadim Gliner, Haifa (IL); Shai Shimon Bard, Zichron Yaakov (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1483 days.

(21) Appl. No.: 14/623,350

(22) Filed: Feb. 16, 2015

(65) Prior Publication Data
US 2016/0235337 A1    Aug. 18, 2016

(51) Int. Cl.
*A61B 5/06* (2006.01)
*A61B 34/20* (2016.01)
*A61M 25/09* (2006.01)
*A61B 5/00* (2006.01)
*A61M 25/01* (2006.01)

(52) U.S. Cl.
CPC ............ *A61B 5/062* (2013.01); *A61B 5/6851* (2013.01); *A61B 34/20* (2016.02); *A61M 25/09* (2013.01); *A61M 25/09041* (2013.01); *A61B 2034/2051* (2016.02); *A61M 2025/0166* (2013.01); *A61M 2025/09083* (2013.01); *A61M 2025/09175* (2013.01); *A61M 2207/00* (2013.01)

(58) Field of Classification Search
CPC ....... A61B 5/062; A61B 5/6851; A61B 34/20; A61B 2034/2051; A61M 25/09; A61M 2207/00; A61M 2025/09083; A61M 2025/09175; A61M 2025/09108; A61M 2025/0166; A61M 25/09041
See application file for complete search history.

(56) References Cited

U.S. PATENT DOCUMENTS 5,372,144 A   12/1994  Mortier et al.
5,386,828 A    2/1995  Owens et al.
(Continued)

FOREIGN PATENT DOCUMENTS

CN    101687087 A    3/2010
CN    101815553 A    8/2010
(Continued)

OTHER PUBLICATIONS

St. Jude Medical CPS Excel ™MediGuide Enabled™ Guidewire and accessories FDA approval document, Section 5-510(k) Summary, May 2012 and FDA letter dated Jun. 2012.
(Continued)

*Primary Examiner* — Amelie R Davis
*Assistant Examiner* — John Denny Li
(74) *Attorney, Agent, or Firm* — Notaro, Michalos & Zaccaria P.C.

(57) ABSTRACT

A guidewire, consisting of a hollow tube, containing a longitudinal lumen and having a spiral channel cut into the tube, and having a distal end. The guidewire has an elongate flexible core positioned within the longitudinal lumen. The guidewire also has a conductive coil, wound around the core at a location within the lumen in proximity to the distal end, that is coupled to output a signal in response to a magnetic field applied to the guidewire.

12 Claims, 3 Drawing Sheets

(56) References Cited

U.S. PATENT DOCUMENTS

| | | | |
|---|---|---|---|
| RE37,148 E * | 4/2001 | Shank | A61M 25/09 604/264 |
| 6,690,963 B2 | 2/2004 | Ben-Haim et al. | |
| 7,317,819 B2 | 1/2008 | Janes | |
| 8,043,351 B2 | 10/2011 | Yon et al. | |
| 8,372,017 B2 | 2/2013 | Schiff et al. | |
| 8,373,017 B2 | 2/2013 | Wu et al. | |
| 8,473,030 B2 | 6/2013 | Greenan et al. | |
| 8,632,468 B2 | 1/2014 | Glossop et al. | |
| 8,636,718 B2 | 1/2014 | Sela et al. | |
| 8,702,626 B1 | 4/2014 | Kim et al. | |
| 8,764,683 B2 | 7/2014 | Meller et al. | |
| 9,002,435 B2 | 4/2015 | Zaslavsky et al. | |
| 2006/0074442 A1 | 4/2006 | Noriega et al. | |
| 2006/0173298 A1 | 8/2006 | Tucker | |
| 2007/0021731 A1 | 1/2007 | Garibaldi et al. | |
| 2009/0247878 A1 * | 10/2009 | Tanioka | A61B 5/0084 600/462 |
| 2009/0326368 A1 | 12/2009 | Zaslavsky et al. | |
| 2011/0130750 A1 | 6/2011 | Ornsby et al. | |
| 2011/0230758 A1 | 9/2011 | Eichler | |
| 2012/0172761 A1 * | 7/2012 | Meller | A61B 5/062 600/585 |
| 2013/0072943 A1 | 3/2013 | Parmar | |
| 2013/0131503 A1 * | 5/2013 | Schneider | A61B 5/066 600/424 |
| 2013/0296692 A1 | 11/2013 | Vanney et al. | |
| 2014/0046216 A1 | 2/2014 | Palme, Jr. et al. | |
| 2016/0113582 A1 * | 4/2016 | Altmann | A61B 5/6858 600/374 |
| 2016/0235337 A1 | 8/2016 | Govari et al. | |
| 2018/0169389 A1 * | 6/2018 | Lemon | A61B 5/042 |

FOREIGN PATENT DOCUMENTS

| | | | |
|---|---|---|---|
| CN | 102639303 A | 8/2012 | |
| CN | 103007417 A | 4/2013 | |
| CN | 104014067 A | 9/2014 | |
| CN | 104271035 A | 1/2015 | |
| EP | 2 085 108 A3 | 12/2009 | |
| JP | 2014042645 A | 3/2014 | |
| WO | 07/25914 A1 | 7/1997 | |
| WO | 2010022370 A1 | 2/2010 | |
| WO | WO 2010022370 A1 * | 2/2010 | A61B 5/042 |
| WO | WO-2010060888 A1 * | 6/2010 | A61M 25/0054 |

OTHER PUBLICATIONS

European Search Report of corresponding application No. EP16155632.9, dated Jul. 8, 2016.

Chinese office action dated Nov. 21, 2019 and search report dated Nov. 12, 2019 for corresponding Chinese application No. 201610086002.6.

Japanese office action for corresponding Japanese application No. 2016-025663, dated Dec. 17, 2019.

* cited by examiner

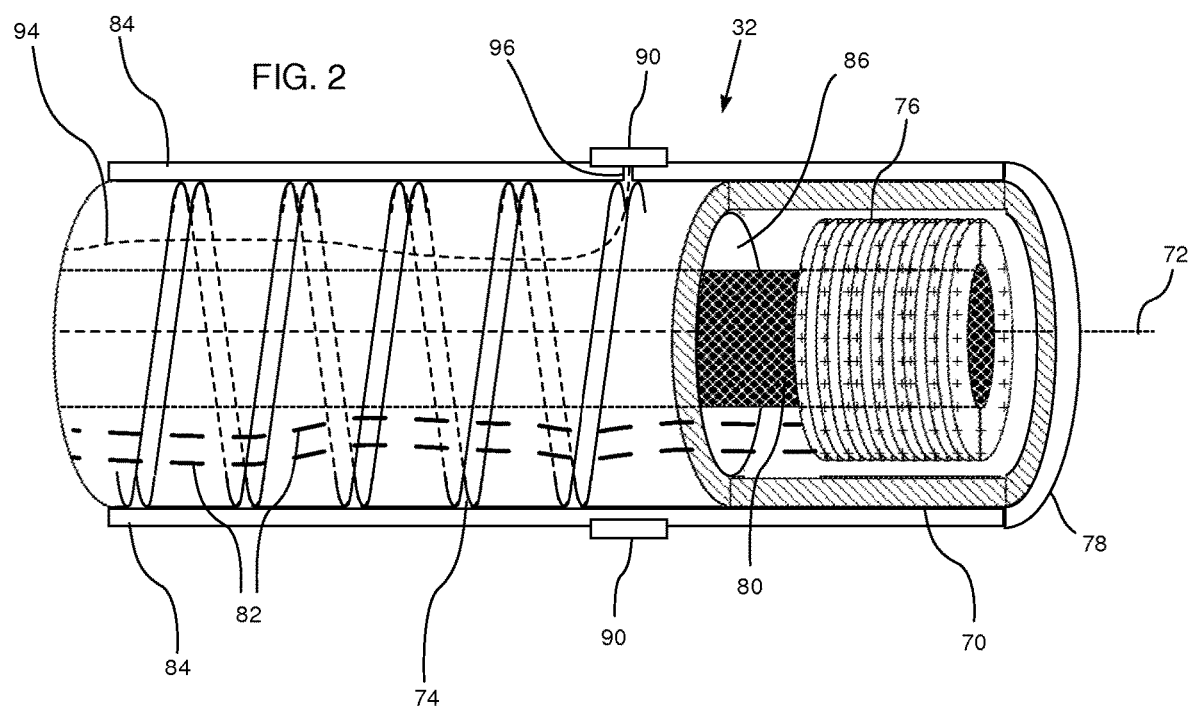

ANGIOPLASTY GUIDEWIRE

CROSS-REFERENCE TO RELATED APPLICATION

This application is related to U.S. patent application titled Navigation of an Angioplasty Guidewire, filed on even date with the present application, and which is incorporated herein by reference.

FIELD OF THE INVENTION

The present invention relates generally to invasive medical procedures, and specifically to a guidewire used in such procedures.

BACKGROUND OF THE INVENTION

Guidewires used in medical procedures have a number of conflicting constraints, such as the requirement the guidewire is sufficiently rigid to enable it to pushed from outside a patient, while being small enough so as to reduce trauma to the patient. A number of different guidewires are known in the art.

U. S. Patent Application 2006/0074442, to Noriega et al., whose disclosure is incorporated herein by reference, describes a guidewire for crossing occlusions or stenosis. The guidewire is stated to be hollow, and has an elongate, tubular guidewire body that has an axial lumen.

U. S. Patent Application 2007/0021731, to Garibaldi et al., whose disclosure is incorporated herein by reference, describes a method for navigating medical devices in body lumens. A guide wire is provided with a magnet on its distal end that can be oriented or oriented and moved by the application of a magnetic field to the magnet.

U. S. Patent Application 2013/0072943, to Parmar, whose disclosure is incorporated herein by reference, describes a system for placing a device enabled for endovascular navigation. A variant of the system is said to comprise a guidewire, for navigating through a patient's vasculature, having electromagnetic (EM) based tracking components at or near the leading end of the guidewire.

U.S. Pat. No. 8,473,030, to Greenan et al., whose disclosure is incorporated herein by reference, describes a vessel position and imaging apparatus. The disclosure refers to an angiographic catheter, and to one or more tracked elements or markers, which are attached to the distal end portion of the catheter by any suitable means.

U.S. Pat. No. 8,372,017, to Schiff et al., whose disclosure is incorporated herein by reference, describes a trackable guidewire. The guidewire is stated to include a plurality of wires arranged in a predetermined pattern to form a body of the guidewire, where the plurality of wires is configured to provide electrical conductivity of signals.

U. S. Patent Application 2014/0046216, to Palme et al., whose disclosure is incorporated herein by reference, describes a guidewire which has a coil with a side of the coil winds having solid physical connections between the coil winds to prevent the connected coil wind side from expanding resulting from the application of force by an actuating member.

U.S. Pat. No. 5,372,144, to Mortier et al., whose disclosure is incorporated herein by reference, describes a medical guidewire which includes a distal end for navigating in a lumen. The distal end comprises a core having a length for navigating the guidewire in the lumen. A formable distal tip is included at the distal end of the core, and a sleeve element substantially surrounds the core over less than a majority of the length of the core. The sleeve element is rotatable with respect to the core, and is offset proximally of the formable distal tip such that the formable distal tip is movable independently of the sleeve element.

U. S. Patent Application 2011/0130750, to Ormsby et al., whose disclosure is incorporated herein by reference, describes an RF ablation system. The disclosure refers to an electromagnetic field generator that generates an electromagnetic field which induces a voltage in a sensor coil of the system. A signal processing unit uses the induced voltage to calculate the position and orientation of a distal end portion or tip of a catheter in a patient's body Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a guidewire, including:

a hollow tube, containing a longitudinal lumen and having a spiral channel cut into the tube, and having a distal end;

an elongate flexible core positioned within the longitudinal lumen; and a conductive coil, wound around the core at a location within the lumen in proximity to the distal end and coupled to output a signal in response to a magnetic field applied to the guidewire.

In a disclosed embodiment the spiral channel includes a continuous helix having a first pitch and a second pitch different from the first pitch.

In a further disclosed embodiment the elongate flexible core includes a wire.

In a yet further disclosed embodiment the guidewire includes an insulating biocompatible sleeve covering the hollow tube. Typically, at least one electrode overlays the insulating sleeve.

In an alternative embodiment the hollow tube is formed of nitinol having an outside diameter of 0.8 mm and an internal diameter of 0.5 mm.

In a further alternative embodiment the conductive coil has an outside diameter of 0.3 mm.

The guidewire may be configured to be inserted into a lumen of a human patient, and the signal may be indicative of a position of the distal end in the lumen of the human patient.

In one embodiment the hollow tube and the conductive coil have a common axis of symmetry.

There is further provided, according to an embodiment of the present invention, a method, including:

cutting a spiral channel in a hollow tube containing a longitudinal lumen, the hollow tube having a distal end;

winding a conductive coil, coupled to output a signal in response to a magnetic field applied to the coil, around an elongate flexible core; and subsequent to the winding, sliding the conductive coil and the elongate flexible core within the longitudinal lumen so as to position the conductive coil in proximity to the distal end.

The present disclosure will be more fully understood from the following detailed description of the embodiments thereof, taken together with the drawings, in which:

BRIEF DESCRIPTION OF THE DRAWINGS

FIG. 2 is a schematic perspective diagram of a distal portion of a guidewire, according to an embodiment of the present invention.

DETAILED DESCRIPTION OF EMBODIMENTS

Overview

Guidewires known in the art may be formed from a wire which is curved into a tight spiral, typically by drawing one side of the wire against a hard surface. The spiral guidewire formed has sufficient flexibility and rigidity so that it can be used in the lumen of a patient as a guidewire. However, the tight spiral form of the guidewire means that there is virtually no "real estate" within the spiral, so that means for tracking the guidewire typically have to be added over the spiral, increasing the dimensions of the guidewire.

Embodiments of the present invention overcome this problem by forming the guidewire from a hollow tube. A spiral channel is cut into the tube, leaving a longitudinal lumen within the tube. The lumen provides the real estate referred to above, and the spiral channel provides the flexibility required for the guidewire. A conductive coil, wound around an elongate flexible core, typically a wire, is located within the lumen in proximity to a distal end of the hollow tube. The coil is coupled to output a signal in response to a magnetic field applied to the guidewire, enabling the distal end of the guidewire to be tracked.

A guidewire implemented in this form allows a functional guidewire to be constructed that is extremely small, while still having internal usable space. For example, in a disclosed embodiment the hollow tube of the guidewire has an outer diameter of approximately 0.8 mm, and an internal diameter of approximately 0.5 mm.

System Description

Figure 1:
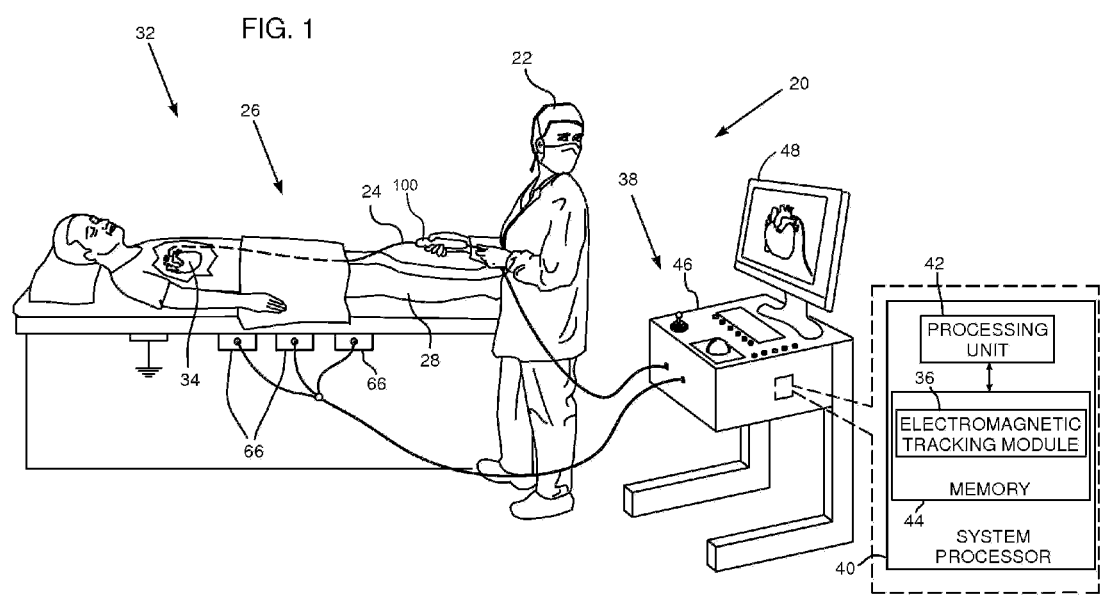
FIG. 1 is a schematic illustration of a guidewire tracking system, according to an embodiment of the present invention.

Reference is now made to FIG. 1, which is a schematic illustration of a guidewire tracking system 20, according to an embodiment of the present invention. For simplicity and clarity, the following description, except where otherwise stated, assumes an angioplasty procedure wherein an operator 22 of system 20, herein assumed to be a medical practitioner, manipulating handle 100, inserts a guidewire 24 into a lumen 26 of a patient 28. The angioplasty procedure may be indicated, for example, for a case of chronic total occlusion. Typically in the procedure, the guidewire is initially inserted into the patient until a distal portion 32 of the guidewire reaches a desired location in, or in proximity to a heart 34 of the patient, after which the guidewire is used to guide surgical apparatus, such as a balloon catheter, to the desired location.

System 20 may be controlled by a system processor 40, comprising a processing unit 42 communicating with a memory 44. Processor 40 is typically mounted in a console 46, which comprises operating controls 38, typically including a pointing device such as a mouse or trackball, that operator 22 uses to interact with the processor. The processor uses software stored in memory 44 to operate system 20.

Results of the operations performed by processor 40 are presented to the operator on a display 48, which typically presents a visual representation of the path taken by guidewire 24 in patient 28. The software may be downloaded to processor 40 in electronic form, over a network, for example, or it may, alternatively or additionally, be provided and/or stored on non-transitory tangible media, such as magnetic, optical, or electronic memory.

For tracking the path of guidewire 24, embodiments of the present invention use an electromagnetic tracking system, similar to that described in U.S. Pat. No. 6,690,963 to Ben-Haim et al., whose disclosure is incorporated herein by reference, and to that used in the Carto™ system produced by Biosense-Webster of Diamond Bar, Calif. The electromagnetic tracking system comprises a plurality of magnetic field generators, herein assumed to comprise three sets of generators 66, each set comprising three orthogonal coils, so that the plurality of generators comprises a total of nine coils. Generators 66 are placed in known locations beneath patient 28, the known locations defining a frame of reference of the generators. A tracking module 36 controls the amplitude and frequency of the alternating magnetic fields produced by the generators.

The alternating magnetic fields interact with a coil, described in more detail below, located within guidewire 24 and at the distal portion of the guidewire, so as to generate alternating electropotentials in the coil, and the electropotentials are received as a signal by tracking module 36. The module, together with processing unit 42, analyzes the received signal, and from the analysis is able to determine a position, i.e., a location and an orientation, of the guidewire coil in the defined frame of reference.

System processor 40 uses the location and orientation of the guidewire coil to track the distal portion of the guidewire. Typically the tracking is presented visually on display 48, for example by incorporating an icon representing the guidewire distal portion into an image of patient 28, as well as a path taken by the icon.

Figure 3A:
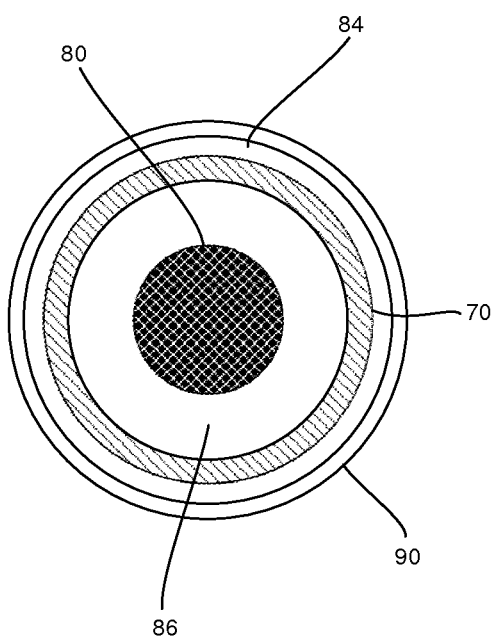
FIGS. 3A and 3B are schematic cross-sections of the guidewire, according to an embodiment of the present invention.
Figure 3B:
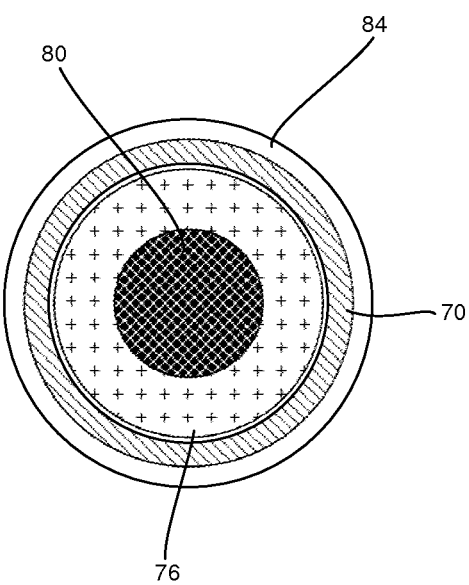

FIG. 2 is a schematic perspective diagram of distal portion 32 of guidewire 24, and FIGS. 3A and 3B are schematic cross-sections of the guidewire, according to an embodiment of the present invention. In FIG. 2, a terminal portion of the distal portion has been cut-away to illustrate the internal structure of the guidewire. Guidewire 24 is formed from a hollow elastic metal tube 70, which has an internal longitudinal lumen 86 and an axis of symmetry 72. In a disclosed embodiment the material of the tube is a nitinol alloy, and the tube has an outer diameter of approximately 0.8 mm. and an inner diameter of approximately 0.5 mm. Tube 70 is formed into a helix, by having a laser cut a spiral channel 74 into the tube. Typically, when the tube is formed by laser cutting of the channel, the pitch of the channel is varied so that there are two or more different pitches. The different pitches give the guidewire the property that it has different flexibilities in different sections of the guidewire.

A small conductive coil 76, made of insulated wire, is inserted into lumen 86 so that it is located at a distal end 78 of the tube. FIG. 3B is a cross-section of guidewire 24 taken at the location of the coil. Prior to insertion the coil is wound on an elongate flexible core 80, herein assumed to comprise a wire, and also referred to herein as wire 80. After the coil has been formed the wire and coil are inserted into lumen 86, so that the wire lies approximately along axis 72, and so that the coil has a common axis of symmetry with axis 72. In the disclosed embodiment referred to above coil 76 has an external diameter of approximately 0.3 mm. Wires 82 connect the two ends of coil 76 to the proximal end of the guidewire, and proximal ends of the wires are connected to tracking module 36 so that the module receives an alternating electropotential signal generated in the coil. Module 36 is able to analyze the signal so as to determine the position of the coil, and thus the position of distal end 78.

The outer surface of tube 70 is covered by a thin layer 84 of biocompatible insulating polymer, the layer acting as a sleeve for the tube. Layer 84 prevents fluids from patient 28 contacting the outer surface of tube 70, and/or penetrating into lumen 86. The layer also acts to mechanically strengthen the guidewire. In some embodiments an electrode 90, typically in the form of a ring, is attached to and overlays layer 84. FIG. 3A is a cross-section of guidewire 24 taken at the location of the electrode. In some embodiments there may be more than one such electrode. An insulated wire 94 feeds from lumen 86, through spiral channel 74 and an aperture 96 formed in layer 84, and connects to the electrode. The wire conveys a signal from the electrode, via the proximal end of the guidewire, to processing unit 42.

Guidewire 24 is typically used to guide a catheter, such as a balloon catheter, to a location in proximity to coil 76, and that has been identified by a signal from the coil.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A guidewire, comprising:
   a hollow tube, containing a longitudinal lumen and having a spiral channel cut into the tube, and having a distal end, and having a length at least long enough to extend from a handle manipulated by an operator to a desired location in or in proximity to a heart of a patient when the guidewire is inserted into the patient to perform a procedure, the spiral channel extending along the length of the hollow tube from at least a first point external to the patient;
   an elongate flexible core positioned within the longitudinal lumen;
   a conductive coil, wound around the core at a core location within the lumen in proximity to the distal end and coupled to output a signal in response to a magnetic field applied to the guidewire;
   an insulating biocompatible sleeve covering the hollow tube; and
   at least one electrode overlaying the insulating sleeve, wherein the electrode is ring-shaped,
   an insulated wire feeding from the lumen, through the spiral channel, wherein the insulated wire connects to the electrode, and the insulated wire conveys at least one signal from the electrode to a processing unit;
   said conductive coil having a first end and a second end, wherein two coil-connecting wires respectively connect the first end and the second end of the conductive coil to a proximal end of the guidewire, wherein said two coil-connecting wires are connected to the electromagnetic tracking system, wherein the electromagnetic tracking system receives an alternating electropotential signal generated in the conductive coil,
   wherein the material of the tube is a nitinol alloy,
   wherein the tube has an outer diameter of 0.8 mm, and an inner diameter of 0.5 mm,
   wherein the tube is formed into a helix,
   wherein the pitch of the channel is varied, wherein there are at least two different pitches,
   wherein the guidewire has different flexibilities in different sections of the guidewire.

2. The guidewire according to claim 1, wherein the elongate flexible core comprises a wire.

3. The guidewire according to claim 1, wherein the conductive coil has an outside diameter of 0.3 mm.

4. The guidewire according to claim 1, wherein the guidewire is configured to be inserted into a lumen of a human patient, and wherein the signal is indicative of a position of the distal end in the lumen of the human patient.

5. The guidewire according to claim 1, wherein the hollow tube and the conductive coil have a common axis of symmetry.

6. The guidewire of claim 1 wherein the spiral channel ends at a second point prior to the core location, such that the distal end of the hollow tube at the core location does not have the spiral channel.

7. A method, comprising:
   cutting a spiral channel in a hollow tube containing a longitudinal lumen, the hollow tube having a distal end, and having a length at least long enough to extend from a handle manipulated by an operator to a desired location in or in proximity to a heart of a patient when the guidewire is inserted into the patient to perform a procedure, the spiral channel extending along the length of the hollow tube from at least a first point external to the patient;
   winding a conductive coil, coupled to output a signal in response to a magnetic field applied to the coil, around an elongate flexible core; and
   subsequent to the winding, sliding the conductive coil and the elongate flexible core within the longitudinal lumen so as to position the conductive coil in proximity to the distal end at a core location;
   covering the hollow tube with an insulating biocompatible sleeve; and
   overlaying the insulating sleeve with at least one electrode, wherein the electrode is ring-shaped,
   feeding an insulated wire from the lumen, through the spiral channel, wherein the insulated wire connects to the electrode, and the insulated wire conveys at least one signal from the electrode to a processing unit,
   said conductive coil having a first end and a second end, wherein two coil-connecting wires respectively connect the first end and the second end of the conductive coil to a proximal end of the guidewire, wherein said two coil-connecting wires are connected to the electromagnetic tracking system, wherein the electromagnetic tracking system receives an alternating electropotential signal generated in the conductive coil,
   wherein the material of the tube is a nitinol alloy,
   wherein the tube has an outer diameter of 0.8 mm, and an inner diameter of 0.5 mm,
   wherein the tube is formed into a helix,
   wherein the pitch of the channel is varied, wherein there are at least two different pitches,
   wherein the guidewire has different flexibilities in different sections of the guidewire.

8. The method according to claim 7, wherein the elongate flexible core comprises a wire.

9. The method according to claim 7, wherein the conductive coil has an outside diameter of 0.3 mm.

10. The method according to claim 7, wherein hollow tube, the elongate flexible core, and the conductive coil are configured as a guidewire for insertion into a lumen of a human patient, and wherein the signal is indicative of a position of the distal end in the lumen of the human patient.

11. The method according to claim 7, wherein the hollow tube and the conductive coil have a common axis of symmetry.

12. The method of claim 7 wherein the spiral channel ends at a second point prior to the core location, such that the distal end of the hollow tube at the core location does not have the spiral channel.

* * * * *